(12) United States Patent
Ye

(10) Patent No.: US 10,556,863 B1
(45) Date of Patent: Feb. 11, 2020

(54) CRYSTALLINE FORM OF (R)-4-HYDROXY-2-OXO-1-PYRROLIDINEACETAMIDE, PREPARATION METHOD THEREFOR AND USE THEREOF

(71) Applicant: CHONGQING RUNZE PHARMACEUTICAL COMPANY LIMITED, Chongqing (CN)

(72) Inventor: Lei Ye, Chongqing (CN)

(73) Assignee: CHONGQING RUZER PHARMACEUTICAL COMPANY LIMITED, Chongqing (CN)

(*) Notice: Subject to any disclaimer, the term of this patent is extended or adjusted under 35 U.S.C. 154(b) by 0 days.

(21) Appl. No.: 16/344,340

(22) PCT Filed: Jul. 7, 2017

(86) PCT No.: PCT/CN2017/092221
§ 371 (c)(1),
(2) Date: Apr. 23, 2019

(87) PCT Pub. No.: WO2018/076784
PCT Pub. Date: May 3, 2018

(30) Foreign Application Priority Data

Oct. 24, 2016 (CN) .......................... 2016 1 0932022

(51) Int. Cl.
*C07D 207/273* (2006.01)

(52) U.S. Cl.
CPC ...... *C07D 207/273* (2013.01); *C07B 2200/13* (2013.01)

(58) Field of Classification Search
CPC ................................................ C07D 207/273
See application file for complete search history.

(56) References Cited

U.S. PATENT DOCUMENTS

| | | | |
|---|---|---|---|
| 4,124,594 A | 11/1978 | Monguzzi | |
| 4,173,569 A | 11/1979 | Banfi | |
| 2019/0256464 A1 | 8/2019 | Ye | |

FOREIGN PATENT DOCUMENTS

| | | | |
|---|---|---|---|
| CN | 102249977 A | 11/2011 | |
| CN | 102442936 A | 5/2012 | |
| CN | 102600130 A | 7/2012 | |
| CN | 102603607 A | 7/2012 | |
| CN | 103553998 A | 2/2014 | |
| CN | 105330582 A | 2/2016 | |
| CN | 105820101 A | 8/2016 | |
| CN | 106166150 A | 11/2016 | |
| KR | 20060010000 | 2/2006 | |
| WO | 2018076782 | 5/2018 | |
| WO | 2018076783 | 5/2018 | |
| WO | 2018076784 | 5/2018 | |
| WO | 2018130063 | 7/2018 | |

OTHER PUBLICATIONS

Almeida, J. et al., "New Enantioselective Synthesis of 4-Hydroxy-2-Oxypyrrolidine-N-Acetamide (Oxiracetam) from Malic Acid", Tethrahedron: Asymmetry, 3(11):1431-40, (1992).
Chen, X. et al., "Synthesis of (R) 4-Hydroxy-Oxo-1-Pyrrolidineacetamide", Fine Chemical Intermediates, 41(5):21-3, (2011).
International Application No. PCT/CN2017/092219; International Search Report (with translation) and Written Opinion of the International Searching Authority, dated Oct. 11, 2017; 9 pages.
International Application No. PCT/CN2017/092220; International Search Report (with translation) and Written Opinion of the International Searching Authority, dated Oct. 11, 2017; 8 pages.
International Application No. PCT/CN2017/092221; International Search Report (with translation) and Written Opinion of the International Searching Authority, dated Sep. 27, 2017; 16 pages.
International Application No. PCT/CN2017/118180; International Search Report (with translation) and Written Opinion of the International Searching Authority, dated Apr. 4, 2018; 12 pages.
Miyamoto, S., "Synthesis of 4-Hydroxy-2-Pyrrolidinone Derivatives", Neurosciences, 11:1-8, (1985).

*Primary Examiner* — Karen Cheng
(74) *Attorney, Agent, or Firm* — Dennis A. Bennett; John Desper

(57) ABSTRACT

A crystalline form of (R)-4-hydroxy-2-oxo-1-pyrrolidineacetamide is disclosed. The crystalline form has a diffraction peak when a diffraction angle, 2θ, is 16.66±0.2°, 17.54±0.20, 21±0.2°, 22.16±0.20, or 30.96±0.20. The crystalline form can be dissolved quickly in water with a solubility greater than or equal to 90 mg/mL, features high bioavailability, has high stability at high temperature, is suitable for preparing multiple pharmaceutical compositions, and can prepare multiple formulations, such as tablets, capsules, dripping pills, sustained-release and controlled-release formulations, and lyophilized powder for injection. The method for preparing the crystalline form is carried out under a mild condition, is easy to operate, introduces a few impurities, and features good reproducibility, an easy-to-control production process and high safety, and is suitable for industrial production.

13 Claims, 1 Drawing Sheet

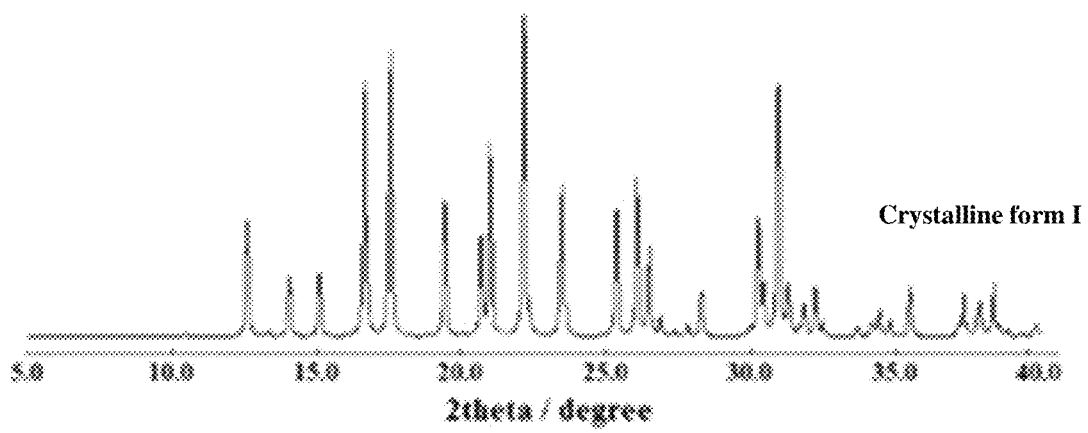

CRYSTALLINE FORM OF (R)-4-HYDROXY-2-OXO-1-PYRROLIDINEACETAMIDE, PREPARATION METHOD THEREFOR AND USE THEREOF

This application is a national stage entry of PCT/CN2017/092221, filed Jul. 7, 2017, which claims priority to Chinese patent application no. 201610932022.0, filed Oct. 24, 2016, the disclosures of which are hereby incorporated by reference as if written herein in their entireties.

TECHNICAL FIELD

The invention relates to (R)-4-hydroxy-2-oxo-1-pyrrolidineacetamide, particularly to a crystalline form of (R)-4-hydroxy-2-oxo-1-pyrrolidineacetamide, preparation method and use thereof.

BACKGROUND ART 4-hydroxy-2-oxo-1-pyrrolidineacetamide, its CAS No. is 62613-82-5, is a new generation of drug for improving cerebral metabolism that was first synthesized in 1974 by SmithKline Beecham Corporation, Italy and has been available on the market in 1987. 4-hydroxy-2-oxo-1-pyrrolidineacetamide is capable of promoting synthesis of phosphorylcholine and phosphoethanolamine, promoting cerebral metabolism, stimulating specific central nervous pathways through blood-brain barrier, and improving intelligence and memory. Studies have shown that its levorotatory form has a better curative effect of promoting brain and intelligence development. In recent years, it has been reported that its dextrorotatory form (R)-4-hydroxy-2-oxo-1-pyrrolidineacetamide has special biological activity in the field of sedation and anti-epilepsy, and has low toxicity and a broad range of pharmaceutical safety. Therefore, (R)-4-hydroxy-2-oxo-1-pyrrolidineacetamide is expected to become an alternative to the existing highly toxic anti-epileptic drugs.

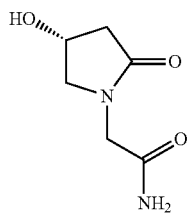

(R)-4-hydroxy-2-oxo-1-pyrrolidineacetamide

In order to effectively develop (R)-4-hydroxy-2-oxo-1-pyrrolidineacetamide into pharmaceutical products, a solid form that is easy to manufacture and has acceptable chemical and physical stability is required to facilitate its processing and circulating storage.

The crystalline solid form is generally superior to the amorphous form in terms of enhancing the purity and stability of the compound. At present, there are few studies on preparation methods and crystalline forms of (R)-4-hydroxy-2-oxo-1-pyrrolidineacetamide, and no crystalline form of (R)-4-hydroxy-2-oxo-1-pyrrolidineacetamide has been disclosed.

SUMMARY OF THE INVENTION

According to a first aspect of the invention, the invention provides a crystalline form of (R)-4-hydroxy-2-oxo-1-pyrrolidineacetamide, and the complete characteristics of the invention are described below, but for convenience, the provided crystalline form of (R)-4-hydroxy-2-oxo-1-pyrrolidineacetamide is referred to as "crystalline form I".

As set forth herein, all the parts are parts by weight, and all the percentages are mass percent, unless otherwise stated.

The object of the invention is achieved by:

a crystalline form I of (R)-4-hydroxy-2-oxo-1-pyrrolidineacetamide having diffraction peaks at diffraction angles 2θ of 16.66±0.2°, 17.54±0.20, 21±0.2°, 22.16±0.2°, and 30.96±0.2°.

The crystalline form I of (R)-4-hydroxy-2-oxo-1-pyrrolidineacetamide of the invention has a relative peak intensity of 100% at the diffraction angle 2θ of 22.16±0.2°; and relative peak intensities of not less than 80% at the diffraction angles 2θ of 17.54±0.20, 16.66±0.2°, and 30.96±0.2°.

The crystalline form I of (R)-4-hydroxy-2-oxo-1-pyrrolidineacetamide of the invention has diffraction peaks at diffraction angles 2θ of 16.66±0.2°, 17.54±0.20, 19.42±0.2°, 21±0.2°, 22.16±0.2°, 23.46±0.2°, 25.36±0.2°, 26.08±0.2°, and 30.96±0.2°.

The crystalline form I of (R)-4-hydroxy-2-oxo-1-pyrrolidineacetamide of the invention has diffraction peaks at diffraction angles 2θ of 12.6±0.2°, 16.66±0.2°, 17.54±0.2°, 19.42±0.2°, 20.68±0.2°, 21±0.2°, 22.16±0.2°, 23.46±0.2°, 25.36±0.2°, 26.08±0.2°, 26.5±0.2°, 30.26±0.2°, and 30.96±0.2°.

The crystalline form I of (R)-4-hydroxy-2-oxo-1-pyrrolidineacetamide of the invention has diffraction peaks at diffraction angles 2θ of 12.6±0.2°, 14.04±0.2°, 15.1±0.2°, 16.66±0.2°, 17.54±0.20, 19.42±0.2°, 20.68±0.2°, 21±0.2°, 22.16±0.2°, 23.46±0.2°, 25.36±0.2°, 26.08±0.2°, 26.5±0.2°, 30.26±0.2°, 30.46±0.2°, 30.96±0.2°, and 31.28±0.2°.

The crystalline form I of (R)-4-hydroxy-2-oxo-1-pyrrolidineacetamide of the invention has a powder diffraction pattern as shown in FIG. 1.

According to a second aspect of the invention, the invention provides a method of preparing the crystalline form I of (R)-4-hydroxy-2-oxo-1-pyrrolidineacetamide, which has a simple process and is suitable for industrial production.

A method of preparing the crystalline form I of (R)-4-hydroxy-2-oxo-1-pyrrolidineacetamide comprises the following steps: dissolving (R)-4-hydroxy-2-oxo-1-pyrrolidineacetamide in an organic solvent to form a supersaturated solution, and then placing the solution in a low temperature environment of from −12° C. to −21° C. to form crystals, filtering the crystals and drying to obtain the crystalline form I of (R)-4-hydroxy-2-oxo-1-pyrrolidineacetamide; the organic solvent is selected from one or more of ethanol, tetrahydrofuran, acetone, methanol, butanone, isoamylol and acetonitrile.

According to an embodiment of the invention, the method of preparing the crystalline form I of (R)-4-hydroxy-2-oxo-1-pyrrolidineacetamide described above comprises the following steps:

adding (R)-4-hydroxy-2-oxo-1-pyrrolidineacetamide into an organic solvent in a concentration of from 5 mg/mL to 55 mg/mL, stirring continuously, dissolving by heating at 35° C. to 95° C., and filtering to form the supersaturated solution; and then sealing the supersaturated solution and cooling it in a low temperature environment of from −12° C. to −21° C. to form the crystals, separating the crystals by filtration, and drying to obtain the crystalline form I of (R)-4-hydroxy-2-oxo-1-pyrrolidineacetamide; the organic solvent is selected from one or more of ethanol, tetrahydrofuran, acetone, methanol, butanone, isoamylol and acetonitrile.

According to an embodiment of the invention, the low temperature environment described above is preferably from −15° C. to −20° C., and more preferably from −17° C. to −19° C.

According to an embodiment of the invention, the method of preparing the crystalline form I of (R)-4-hydroxy-2-oxo-1-pyrrolidineacetamide described above comprises the following steps: adding the (R)-4-hydroxy-2-oxo-1-pyrrolidineacetamide into an organic solvent in a concentration of from 5 mg/mL to 50 mg/mL, stirring continuously, dissolving by heating at from 45° C. to 75° C., and filtering to form the supersaturated solution; and then sealing the supersaturated solution and cooling it in a low temperature environment of from −17° C. to −19° C. to form crystals, separating the crystals by filtration, and drying at 65° C. to 75° C. and 0-30% relative humidity for 4-6 h, to obtain the crystalline form I of (R)-4-hydroxy-2-oxo-1-pyrrolidineacetamide; the organic solvent is selected from one or more of ethanol, tetrahydrofuran, acetone, methanol, butanone, isoamylol and acetonitrile.

The raw (R)-4-hydroxy-2-oxo-1-pyrrolidineacetamide of the invention can be a commercially available product or can be self-made, and the remaining raw materials or reagents are all commercially available products. In the preparation of the crystalline form of the invention, the stirring is a conventional manner well known in the art, and the filtration is a conventional solid-liquid separation method well known in the art.

According to a third aspect of the invention, the invention provides use of the crystalline form I of (R)-4-hydroxy-2-oxo-1-pyrrolidineacetamide (in a therapeutically effective amount) for manufacturing a medicament for preventing or treating epilepsy. The invention provides use of the crystalline form I of (R)-4-hydroxy-2-oxo-1-pyrrolidineacetamide for the preparation of anti-epileptic drugs for preventing or treating acute seizures of epilepsy, in particular for the preparation anti-epileptic drugs for preventing or treating acute and severe seizures of epilepsy. The invention provides use of the crystalline form I of (R)-4-hydroxy-2-oxo-1-pyrrolidineacetamide for the preparation of anti-epileptic drugs for preventing or treating generalized seizures of epilepsy. The invention provides use of the crystalline form I of (R)-4-hydroxy-2-oxo-1-pyrrolidineacetamide for the preparation of anti-epileptic drugs for preventing or treating partial seizures of epilepsy. The invention provides use of the crystalline form I of (R)-4-hydroxy-2-oxo-1-pyrrolidineacetamide for the preparation of anti-epileptic drugs for preventing or treating status epilepticus. The crystalline form I of (R)-4-hydroxy-2-oxo-1-pyrrolidineacetamide of the invention exhibits special pharmacological activities in stabilization of abnormal cerebral discharge, sedation, anti-epilepsy, and the like; and it has solubility of more than or equal to 90 mg/mL in water, and a high bioavailability.

According to a fourth aspect of the invention, the invention provides a pharmaceutical composition comprising the crystalline form I of (R)-4-hydroxy-2-oxo-1-pyrrolidineacetamide described above, and pharmaceutically acceptable excipients. The composition is in any clinically acceptable pharmaceutical dosage form, including tablets, powders, granules, injections, capsules, dripping pills, sustained release formulations, and lyophilized powders for injection for administrations including (but not limited to) oral, rectal, transvaginal, nasal, inhalation, topical (including transdermal) or parenteral administration.

Advantageous Effects

The invention provides a crystalline form of (R)-4-hydroxy-2-oxo-1-pyrrolidineacetamide having diffraction peaks at diffraction angles 2θ of 16.66±0.2°, 17.54±0.20, 21±0.2°, 22.16±0.2°, and 30.96±0.2°, and having a relative peak intensity of 100% at the diffraction angle 2θ of 22.16±0.2°; and relative peak intensities of not less than 80% at the diffraction angles 2θ of 17.54±0.2°, 16.66±0.20, and 30.96±0.20. The crystalline form I of (R)-4-hydroxy-2-oxo-1-pyrrolidineacetamide of the invention exhibits special pharmacological activities in stabilization of abnormal cerebral discharge, sedation, anti-epilepsy, and the like. The crystalline form I of (R)-4-hydroxy-2-oxo-1-pyrrolidineacetamide of the invention has a high dissolution velocity in water, solubility of more than or equal to 90 mg/mL in water, and a high bioavailability. The crystalline form I of (R)-4-hydroxy-2-oxo-1-pyrrolidineacetamide of the invention does not show a phenomenon of crystal transformation at between 30° C. and 80° C., and has good stability in high temperatures. When the crystalline form I of (R)-4-hydroxy-2-oxo-1-pyrrolidineacetamide of the invention is used for storage or formulation processing, the requirements on processing and storage temperatures are lower. The crystalline form I of (R)-4-hydroxy-2-oxo-1-pyrrolidineacetamide of the invention has good fluidity and good solubility in conventional solvents (such as water, methanol, DMSO, or the like), and the formulation process has a high adaptability. The crystalline form I of (R)-4-hydroxy-2-oxo-1-pyrrolidineacetamide of the invention is suitable for producing a variety of pharmaceutical compositions, which can be made into pharmaceutical preparations such as tablets, capsules, dripping pills, sustained release formulations, lyophilized powders for injection, and the like. The preparation method of the invention adopts cheap and easily available raw material, and the prepared crystalline form I of (R)-4-hydroxy-2-oxo-1-pyrrolidineacetamide has a high purity. The preparation method requires mild conditions and simple operations, introduces a low level of impurities and has a good reproducibility; the production process is easy to control, has a high safety, and is suitable for industrial production.

BRIEF DESCRIPTION OF THE DRAWING

FIG. 1 is a powder diffraction pattern of the crystalline form I of (R)-4-hydroxy-2-oxo-1-pyrrolidineacetamide.

DEFINITIONS

When describing the compound, crystalline form, uses, compositions and methods of the invention, the following terms have the following meanings, unless otherwise stated.

The term "therapeutically effective amount" means an amount that is sufficient to effect treatment when the amount is administered to a patient in need of treatment. As used herein, the term "treating" means treating a disease, illness or medical condition of a patient, for example, mammal (particularly human), comprising:

(a) preventing the occurrence of the disease, illness or medical condition, namely preventive treatment of the patient;

(b) improving the disease, illness or medical condition, namely eliminating or regressing the disease, illness or medical condition of the patient, including counteracting effects of other therapeutic agents;

(c) inhibiting the disease, illness or medical condition, namely mitigating or prohibiting the development of the disease, illness or medical condition of the patient; or (d) alleviating the symptoms of the disease, illness or medical condition of the patient.

It is noted that the singular form "a(n)", "one" and "the", as in the specification and the appended claims, can include plural referents, unless otherwise clearly stated in the content.

DETAILED DESCRIPTION OF THE PREFERRED EMBODIMENTS

The invention is described in detail by the following examples. It should be pointed out that the following examples are intended to illustrate the invention, and are not to be construed as limiting the scope of the invention. Some non-essential modifications and adjustments to the invention can be made by those skilled in the art according to the aforementioned summary of the invention.

Preparation of crystalline form I of (R)-4-hydroxy-2-oxo-1-pyrrolidineacetamide

Example 1

30 mg of (R)-4-hydroxy-2-oxo-1-pyrrolidineacetamide (Chongqing Runze Pharmaceutical Co., Ltd.) was dissolved in 2 mL of isoamylol, heated at 50° C., and filtered to obtain a supersaturated solution. The solution was sealed and placed at −19° C. for 24 h for cooling crystallization, separated by filtration and dried at 70° C. and 20% relative humidity for approximately 5 h, and obtained crystals.

Example 2

The crystallographic parameters of the crystals of (R)-4-hydroxy-2-oxo-1-pyrrolidineacetamide obtained in Example 1 were measured.

Powder Diffraction Measurement (XRPD):

Instrument and condition for measurement: the measurement was performed using the Bruker D2 PHASER powder diffractometer at room temperature. The measurement conditions were: Cu Kα (1.5418 Å) radiation as the light source, a voltage of 30 kV, a current of 10 mA, a test step length of 0.014°, a scanning rate of 0.1 s/step, and a scanning range of 5-40° (2θ). According to the measurement, the crystals of (R)-4-hydroxy-2-oxo-1-pyrrolidineacetamide prepared in Example 1 have diffraction peaks at diffraction angles 2θ of 12.6±0.2°, 14.04±0.2°, 15.1±0.2°, 16.66±0.2°, 17.54±0.20, 19.42±0.2°, 20.68±0.2°, 21±0.2°, 22.16±0.2°, 23.46±0.2°, 25.36±0.2°, 26.08±0.2°, 26.5±0.2°, 30.26±0.2°, 30.46±0.2°, 30.96±0.20, and 31.28±0.20. For convenience, the crystals are referred to as "crystalline form I of (R)-4-hydroxy-2-oxo-1-pyrrolidineacetamide", the powder diffraction pattern thereof is shown in FIG. 1, and the analysis of diffraction data is presented as Table 1 below.

TABLE 1

Powder diffraction peaks of crystalline form I
Crystalline form I of (R)-4-hydroxy-2-oxo-1-pyrrolidineacetamide

| Dihedral angle (°) | Intensity (I) |
|---|---|
| 10.46 | 9.39656 |
| 12.6 | 59.8573 |
| 13.36 | 12.6306 |
| 14.04 | 43.3195 |
| 15.1 | 44.5687 |
| 16.66 | 89.2818 |
| 17.54 | 94.3077 |
| 18.7 | 6.15941 |
| 18.98 | 7.29838 |
| 19.42 | 65.1718 |
| 20 | 11.3961 |
| 20.68 | 56.0607 |
| 21 | 78.0294 |
| 22.16 | 100 |
| 23.46 | 68.952 |
| 25.36 | 62.6536 |
| 26.08 | 70.2268 |
| 26.5 | 53.3187 |
| 26.9 | 25.4565 |
| 27.34 | 14.2533 |
| 27.82 | 20.2795 |
| 28.3 | 37.6658 |
| 29.98 | 19.0168 |
| 30.26 | 60.6457 |
| 30.46 | 41.6412 |
| 30.96 | 88.6258 |
| 31.28 | 40.9662 |

As can be seen from Table 1 above, the crystalline form I of (R)-4-hydroxy-2-oxo-1-pyrrolidineacetamide of the invention has a relative peak intensity of 100% at the diffraction angle 2θ of 22.16±0.2°; and relative peak intensities of not less than 80% at the diffraction angles 2θ of 17.54±0.20, 16.66±0.2°, and 30.96±0.2°.

Single Crystal X-Ray Diffraction (SXRD) Measurement:

The used instrument was X-ray single crystal diffractometer (Gemini A Ultra, Agilent Inc., USA) with Cu Kα radiation at Emission λ=1.5418 Å, and the data were collected using ω/2θ scan. Data restoration and absorption correction were performed using CrysAlis PRO software. The space group was determined by extinction law of the system, and verified by the refinement results. Using SHELXS-97 program, the crystal structure was solved by the direct method, and the results were corrected by full-matrix least squares method, the coordinates of the hydrogen atoms on carbons were input according to the theoretical calculation, and the coordinates of the hydrogen atoms on the other atoms were input according to calculation by electron density map. The crystallographic parameters of the crystalline form I of (R)-4-hydroxy-2-oxo-1-pyrrolidineacetamide of the invention are shown in Table 2 below.

Table 2. Crystal Data and Structure Refinement for Exp_9533

Identification code exp_9533
Empirical formula C12H20N4O6
Formula weight 316.32
Measurement temperature 293(2) K
Wavelength 1.54184 A
Crystal system, space group Monoclinic, P $2_1$
Unit cell dimensions a=6.7856(2) A alpha=90 deg.
   b=12.6010(4) A beta=102.471(4) deg.
   c=8.6586(3) A gamma=90 deg.
Unit cell volume 722.90(4) A^3
Z, Calculated density 2, 1.453 Mg/m^3
Absorption coefficient 0.998 mm^−1
Structure factor F(000) 336
Crystal size 0.10×0.05×0.03 mm
Theta range for date collection 5.23 to 63.69 deg.

Crystal surface index range (Limiting indices) -7<=h<=7, -14<=k<=14, -10<=l<=10

Total number of diffraction points/Number of independent diffraction points (Reflections collected/unique) 12614/2378 [R(int)=0.04841

Completeness to theta=63.69 100.0%

Absorption correction Semi-empirical from equivalents

Max. and min transmission 0.9707 and 0.9068

Refinement method Full-matrix least-squares on F^2

Independent diffraction point data/restraints/refinement parameters (data/restraints/parameters) 2378/1/201

Goodness of fit factor GOOF value (Goodness-of-fit on F^2) 0.985

R indices [I>2σ(I)]* (Final R indices [I>2sigma(I)I) R1=0.0329, wR2=0.0763

R indices (all data) R1=0.0380, wR2=0.0803

Absolute structure parameter 0.1(2)

Maximum residual electron peak/hole (Largest diff. peak and hole) 0.141 and -0.163 e.A^-3

*$R_1=\Sigma||F_o|-|F_c||/\Sigma|F_o|$, $wR_2=[\Sigma w(F_o^2-F_c^2)^2/\Sigma w(F_o^2)^2]^{1/2}$, $w=[\sigma^2(F_o)^2+(0.1(\max(0, F_o^2)+2F_c^2)/3^2]^{-1}$ As can be seen from the Table 2 above, the crystalline form I of the (R)-4-hydroxy-2-oxo-1-pyrrolidineacetamide of the invention is a monoclinic system Monolinic, P2$_1$, where, a=6.7856(2) A alpha=90 deg.; b=12.6010(4)A beta=102.471(4) deg.; and c=8.6586(3)A gamma=90 deg.

Referring to Example 1, the crystalline form I of (R)-4-hydroxy-2-oxo-1-pyrrolidineacetamide was prepared according to Examples 3-10.

Example 3

30 mg of (R)-4-hydroxy-2-oxo-1-pyrrolidineacetamide was dissolved in 4 mL of acetonitrile, heated at 55° C., and filtered to obtain a supersaturated solution. The solution was sealed and placed at -17° C. for 3 h for cooling crystallization, separated by filtration and dried at 65° C. and 30% relative humidity for approximately 4 h, and obtained colorless, sandy crystals. The crystals were identified as a crystalline form I of (R)-4-hydroxy-2-oxo-1-pyrrolidineacetamide by using the method in Example 2.

Example 4

60 mg of (R)-4-hydroxy-2-oxo-1-pyrrolidineacetamide was dissolved in 10 mL of ethanol, heated at 40° C., and filtered to obtain a supersaturated solution. The solution was sealed and placed at -20° C. for 24 h for cooling crystallization, separated by filtration and dried at 75° C. and 10% relative humidity for approximately 6 h, and obtained colorless, sandy crystals. The crystals were identified as a crystalline form I of (R)-4-hydroxy-2-oxo-1-pyrrolidineacetamide by using the method in Example 2.

Example 5

60 mg of (R)-4-hydroxy-2-oxo-1-pyrrolidineacetamide was dissolved in 2 mL of isoamylol, heated at 75° C., and filtered to obtain a supersaturated solution. The solution was sealed and placed at -12° C. for 36 h for cooling crystallization, separated by filtration and dried at 50° C. and 30% relative humidity for approximately 5 h, and obtained colorless, sandy crystals. The crystals were identified as a crystalline form I of (R)-4-hydroxy-2-oxo-1-pyrrolidineacetamide by using the method in Example 2.

Example 6

30 mg of (R)-4-hydroxy-2-oxo-1-pyrrolidineacetamide was dissolved in 4 mL of isoamylol, heated at 65° C., and filtered to obtain a supersaturated solution. The solution was sealed and placed at -21° C. for 36 h for cooling crystallization, separated by filtration and dried at 75° C. and 40% relative humidity for approximately 3 h, and obtained colorless, sandy crystals. The crystals were identified as a crystalline form I of (R)-4-hydroxy-2-oxo-1-pyrrolidineacetamide by using the method in Example 2.

Example 7

100 mg of (R)-4-hydroxy-2-oxo-1-pyrrolidineacetamide was dissolved in 2 mL of tetrahydrofuran, heated at 45° C., and filtered to obtain a supersaturated solution. The solution was sealed and placed at -18° C. for 36 h for cooling crystallization, separated by filtration and dried at 70° C. and 15% relative humidity for approximately 8 h, and obtained colorless, sandy crystals. The crystals were identified as a crystalline form I of (R)-4-hydroxy-2-oxo-1-pyrrolidineacetamide by using the method in Example 2.

Example 8

80 mg of (R)-4-hydroxy-2-oxo-1-pyrrolidineacetamide was dissolved in 2 mL of acetone, heated at 45° C., and filtered to obtain a supersaturated solution. The solution was sealed and placed at -19° C. for 36 h for cooling crystallization, separated by filtration and dried at 75° C. and 20% relative humidity for approximately 6 h, and obtained colorless, sandy crystals. The crystals were identified as a crystalline form I of (R)-4-hydroxy-2-oxo-1-pyrrolidineacetamide by using the method in Example 2.

Example 9

330 mg of (R)-4-hydroxy-2-oxo-1-pyrrolidineacetamide was dissolved in 6 mL of methanol, heated at 45° C., and filtered to obtain a supersaturated solution. The solution was sealed and placed at -19° C. for 36 h for cooling crystallization, separated by filtration and dried at 75° C. and 25% relative humidity for approximately 6 h, and obtained colorless, sandy crystals. The crystals were identified as a crystalline form I of (R)-4-hydroxy-2-oxo-1-pyrrolidineacetamide by using the method in Example 2.

Example 10

30 mg of (R)-4-hydroxy-2-oxo-1-pyrrolidineacetamide was dissolved in 5 mL of butanone, heated at 40° C., and filtered to obtain a supersaturated solution. The solution was sealed and placed at -19° C. for 48 h for cooling crystallization, separated by filtration and dried at 65° C. and 15% relative humidity for approximately 5 h and obtained colorless, sandy crystals. The crystals were identified as a crystalline form I of (R)-4-hydroxy-2-oxo-1-pyrrolidineacetamide by using the method in Example 2.

Performance Measurement Experiment of
Crystalline Form I of
(R)-4-Hydroxy-2-Oxo-1-Pyrrolidineacetamide Example 11

The crystalline form I of (R)-4-hydroxy-2-oxo-1-pyrrolidineacetamide of the invention was placed on a single crystal silicon sample stage, heated from 30° C. to 80° C., and subjected to powder X-ray diffraction measurement at 35° C., 45° C., 55° C., 65° C. and 75° C., respectively. The test results show that the crystalline form I of (R)-4-hydroxy-2-oxo-1-pyrrolidineacetamide of the invention does not exhibit crystal transformation phenomenon between 30° C. and 80° C. It can be seen that the crystalline form I of (R)-4-hydroxy-2-oxo-1-pyrrolidineacetamide of the invention has good stability at high temperatures. When the crystalline form I of (R)-4-hydroxy-2-oxo-1-pyrrolidineacetamide of the invention is used for storage or formulation processing, the requirements on processing and storage temperatures are reduced.

Preparation of Compositions Comprising
Crystalline Form I of
(R)-4-Hydroxy-2-Oxo-1-Pyrrolidineacetamide Example 12

1000 capsules comprising crystalline form I of (R)-4-hydroxy-2-oxo-1-pyrrolidineacetamide were taken as examples, which were prepared by using 180 mg/capsule of the crystalline form I of (R)-4-hydroxy-2-oxo-1-pyrrolidineacetamide prepared by the method in Example 1, 90.8 mg/capsule of lactose, 82 mg/capsule of sodium carboxymethyl starch, 7.2 mg/capsule of talcum powder, and an appropriate amount of 10% polyvinylpyrrolidone. The specific preparation method was given as follows: the raw materials and excipients were firstly passed through an 80-mesh sieve; the above-mentioned amounts of crystalline form I of (R)-4-hydroxy-2-oxo-1-pyrrolidineacetamide, lactose and sodium carboxymethyl starch were weighed and mixed uniformly, and 10% PVP ethanol solution was added to produce a soft material, pelletized, dried and granulated; the above-mentioned amount of talcum powder was added to the granules, mixed uniformly and filled into the capsules.

Example 13

60 g of the crystalline form I of (R)-4-hydroxy-2-oxo-1-pyrrolidineacetamide prepared by the method in Example 1 and 140 g of glucose were dissolved with 500 ml of water for injection in a mixing equipment under controlling the temperature between 50° C. and 58° C., and stirred until completely dissolved. The solution was cooled to 25° C. The activated carbon was added into the above prepared solution for decolorization, and then the activated carbon was removed by filtration. Phosphate buffer was added to adjust pH of the solution to 4.0, followed by adding water for injection to 5000 ml, filing and sealing, sterilizing at 105° C. for 30 min, and obtained an injection.

Example 14

1000 tablets comprising crystalline form I of (R)-4-hydroxy-2-oxo-1-pyrrolidineacetamide were taken as examples, which were prepared by using 200 mg/tablet of the crystalline form I of (R)-4-hydroxy-2-oxo-1-pyrrolidineacetamide prepared by the method in Example 1, 44 mg/tablet of starch, 50 mg/tablet of microcrystalline cellulose, 6 mg/table of talcum powder and an appropriate amount of 2% hydroxypropyl methylcellulose (K4M). The specific preparation method was given as follows: the raw materials and excipients were firstly passed through an 80-mesh sieve; the above-mentioned amounts of crystalline form I of (R)-4-hydroxy-2-oxo-1-pyrrolidineacetamide, starch and microcrystalline cellulose were weighed and mixed uniformly, and an appropriate amount of 2% HPMC aqueous solution was added to produce a soft material, pelletized, dried and granulated; the prescription amount of talcum powder was added to the granules, mixed uniformly and pressed into the tablets.

The invention claimed is:

1. A crystalline form I of (R)-4-hydroxy-2-oxo-1-pyrrolidineacetamide having diffraction peaks at diffraction angles 2θ of 16.66±0.2°, 17.54±0.2°, 21±0.2°, 22.16±0.2°, and 30.96±0.2°.

2. The crystalline form I of (R)-4-hydroxy-2-oxo-1-pyrrolidineacetamide according to claim 1, characterized in that the crystalline form I of (R)-4-hydroxy-2-oxo-1-pyrrolidineacetamide has diffraction peaks at diffraction angles 2θ of 16.66±0.2°, 17.54±0.2°, 19.42±0.2°, 21±0.2°, 22.16±0.2°, 23.46±0.2°, 25.36±0.2°, 26.08±0.2°, and 30.96±0.2°.

3. The crystalline form I of (R)-4-hydroxy-2-oxo-1-pyrrolidineacetamide according to claim 1, characterized in that the crystalline form I of (R)-4-hydroxy-2-oxo-1-pyrrolidineacetamide has a relative peak intensity of 100% at the diffraction angle 2θ of 22.16±0.2°; and relative peak intensities of not less than 80% at the diffraction angles 2θ of 17.54±0.2°, 16.66±0.2°, and 30.96±0.2°.

4. The crystalline form I of (R)-4-hydroxy-2-oxo-1-pyrrolidineacetamide according to claim 1, characterized in that the crystalline form I of (R)-4-hydroxy-2-oxo-1-pyrrolidineacetamide has diffraction peaks at diffraction angles 2θ of 12.6±0.2°, 16.66±0.2°, 17.54±0.2°, 19.42±0.2°, 20.68±0.2°, 21±0.2°, 22.16±0.2°, 23.46±0.2°, 25.36±0.2°, 26.08±0.2°, 26.5±0.2°, 30.26±0.2°, and 30.96±0.2°.

5. The crystalline form I of (R)-4-hydroxy-2-oxo-1-pyrrolidineacetamide according to claim 1, characterized in that the crystalline form I of (R)-4-hydroxy-2-oxo-1-pyrrolidineacetamide has diffraction peaks at diffraction angles 2θ of 12.6±0.2°, 14.04±0.2°, 15.1±0.2°, 16.66±0.2°, 17.54±0.20, 19.42±0.2°, 20.68±0.2°, 21±0.2°, 22.16±0.2°, 23.46±0.2°, 25.36±0.2°, 26.08±0.2°, 26.5±0.2°, 30.26±0.2°, 30.46±0.2°, 30.96±0.2°, and 31.28±0.2°.

6. The crystalline form I of (R)-4-hydroxy-2-oxo-1-pyrrolidineacetamide according to claim 1, characterized in that the crystalline form I has a powder diffraction pattern as shown in FIG. 1.

7. A method of preparing the crystalline form I of (R)-4-hydroxy-2-oxo-1-pyrrolidineacetamide according to claim 1, applying the following steps: dissolving (R)-4-hydroxy-2-oxo-1-pyrrolidineacetamide in an organic solvent to form a supersaturated solution, and then placing the solution in a low temperature environment of from −12° C. to −21° C. to form crystals, separating the crystals by filtration and drying to obtain the crystalline form I of (R)-4-hydroxy-2-oxo-1-pyrrolidineacetamide; the organic solvent is selected from one or more of ethanol, tetrahydrofuran, acetone, methanol, butanone, isoamylol and acetonitrile.

8. The method according to claim 7, characterized in that the method applies the following steps: adding (R)-4-hydroxy-2-oxo-1-pyrrolidineacetamide into an organic solvent in a concentration of from 10 mg/mL to 55 mg/mL, stirring continuously, dissolving by heating at 35° C. to 90° C., and filtering to form the supersaturated solution; then sealing the supersaturated solution and placing it in a low temperature environment of from −12° C. to −21° C. to form crystals, separating the crystals by filtration, and drying to obtain the crystalline form I of (R)-4-hydroxy-2-oxo-1-pyrrolidineacetamide; the organic solvent is selected from one or more of ethanol, tetrahydrofuran, acetone, methanol, butanone, isoamylol and acetonitrile.

9. The method according to claim 7, characterized in that the low temperature environment is from −17° C. to −19° C.

10. The method according to claim 8, characterized in that the low temperature environment is from −17° C. to −19° C.

11. A method for alleviating the symptoms of epilepsy in a patient in need thereof comprising: administering the crystalline form I of (R)-4-hydroxy-2-oxo-1-pyrrolidineacetamide according to claim 1.

12. The method of claim 11, wherein the crystalline form I of (R)-4-hydroxy-2-oxo-1-pyrrolidineacetamide is administered in the form of a pharmaceutical composition comprising the crystalline form I of (R)-4-hydroxy-2-oxo-1-pyrrolidineacetamide, and pharmaceutically acceptable excipients.

13. The method according to claim 12, characterized in that the composition is tablets, powders, granules, injections, capsules, dripping pills, sustained release formulations, or lyophilized powders for injection.

\* \* \* \* \*